United States Patent [19]

Weber

[11] 4,045,175
[45] Aug. 30, 1977

[54] MICRO-METHOD OF ERYTHROCYTE SEDIMENTATION

[76] Inventor: Ragnar Weber, No. 67, Rainweg, 6904 Ziegelhausen, Germany

[21] Appl. No.: 639,323

[22] Filed: Dec. 10, 1975

[51] Int. Cl.² ............................................. G01N 33/16
[52] U.S. Cl. ................................................ 23/230 B
[58] Field of Search ................ 23/230 B, 253 R, 259; 128/2 G, 2 M; 73/61.4

[56] References Cited

U.S. PATENT DOCUMENTS

| | | | |
|---|---|---|---|
| 2,102,785 | 12/1937 | Brooks | 23/253 R X |
| 3,734,079 | 5/1973 | Weber | 23/253 R X |
| 3,898,982 | 8/1975 | Katsuda | 23/253 R X |
| 3,910,103 | 10/1975 | Rose | 23/230 B X |

OTHER PUBLICATIONS

*Gradwohl's Clinical Laboratory Methods & Diagnosis*, 7th ed., vol. 1, Mosby Co., St. Louis (1970); pp. 496–498.
*Aloe Scientific Laboratory Apparatus–Equipment–Reagents*, Catalog No. 103 (1952); pp. 103 and 105.

*Primary Examiner*—Robert M. Reese
*Attorney, Agent, or Firm*—John C. Smith, Jr.

EXEMPLARY CLAIM

The micro-method of erythrocyte sedimentation comprises using capillary glass tubes provided with an anticoagulant coating on their inner surface.

1 Claim, 2 Drawing Figures

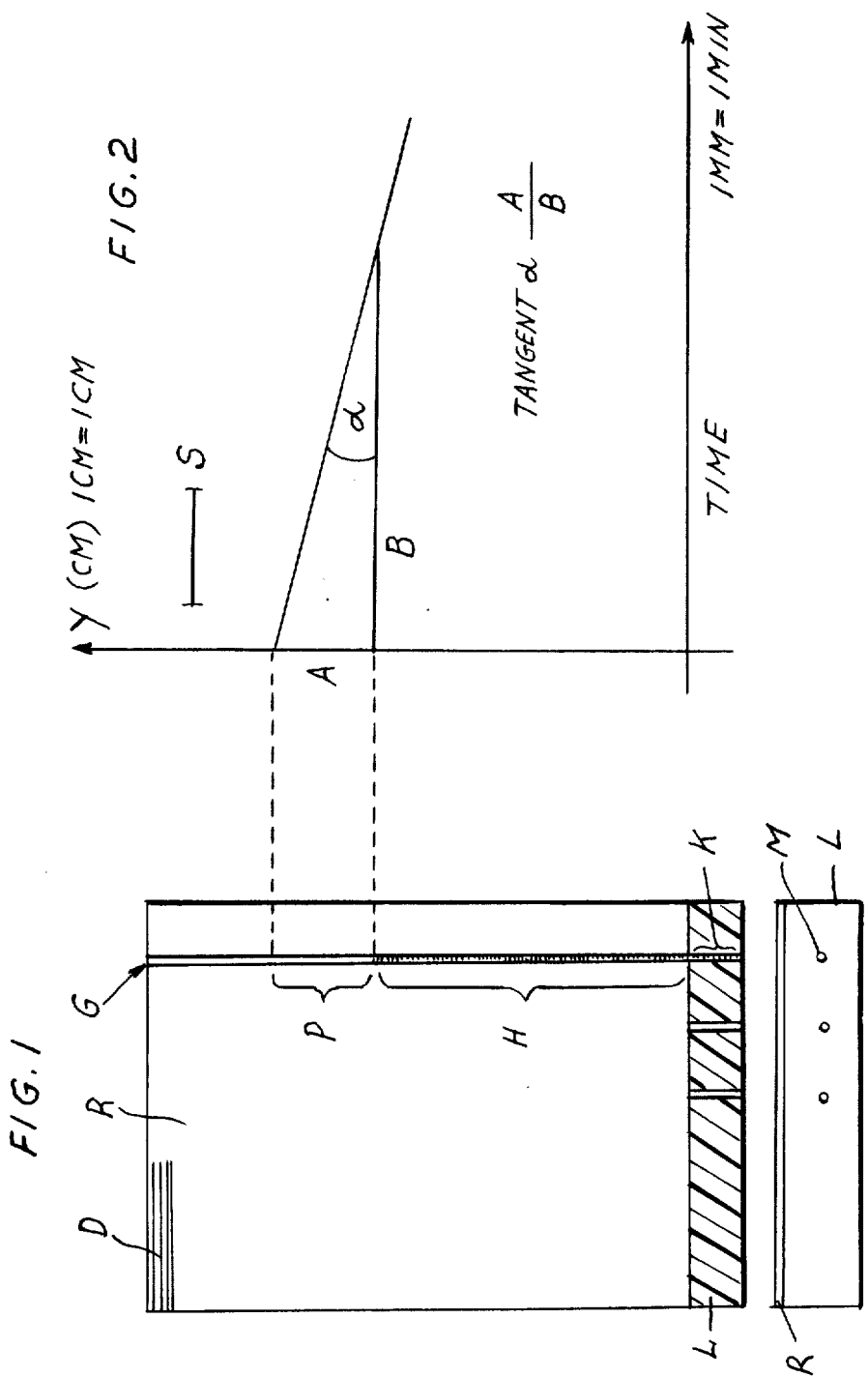

MICRO-METHOD OF ERYTHROCYTE SEDIMENTATION

BACKGROUND OF THE INVENTION

This invention relates to a micro-method of erythrocyte sedimentation.

Of the micro-methods of erythrocyte sedimentation, the method according to Pantschenkoff was being used for some time. The principle of this method consisted in making the blood non-coagulatable by the addition of sodium citrate. Values were determined and judged after 1 and 2 hours, just as with the macro-method according to Westergreen, which is based on the same principle. Both points of measurement corresponding to points of a line possessing substantial curvature, are compared after 1 to 2 hours with emperical values within a substantial range of scatter.

(See:
Rau, "Deutsche Medizinische Wochenschrift", 1931 II, page 1410;
Wail, "Jahrbuch der Kinderheilkunde", 115, 1927, page 79;
Reichel, "Blutkoerperchensenkung", Vienna 1936;
Klima, R. and Bodart "Blutkoerperchensenkung, Koagulationsband und Blutbild als allgemeine Krankheitsreaktion feur die Klinik und Praxis", Vienna 1947;
Hallmann, "Klinische Chemie und Mikroskopie", 7th edition, Stuttgart 1955, pages 356-360.)

A micro-method of erythrocyte sedimentation has not so far prevailed, and the macro-method of erythrocyte sedimentation according to Westergreen is most commonly used. Both the micro- and macro-methods used so far for erythrocyte sedimentation require too many steps which, together with the possibly inexact dilution with sodium citrate, lead to substantial errors. Final judgement is only possible after 2 hours. The ratio between the 1- and 2-hour values enables only a very rough orientation.

SUMMARY OF THE INVENTION

It is therefore the object of the invention to avoid these disadvantages and to provide a simple and exact micro-method of erythrocyte sedimentation, in which venipuncture is avoided, since especially with the treatment of children technical and psychological difficulties arise during blood collection, a few drops of blood, which can easily be collected from a capillary region, suffice for carrying through the method, and the evaluation can be quickly performed.

To attain this object the present invention provides a micro-method of erythrocyte sedimentation which comprises using capillary glass tubes provided with an anti-coagulant coating on their inner surface. For this micro-method of erythrocyte sedimentation there may be used e.g. heparinized capillary tubes as known from the microdetermination of haematocrit.

It is surprising for the specialist skilled in the art that the graphic representation of the settling data measured continuously from the erythrocyte column is a curve which nearly corresponds to a straight line. If this curve is replaced by a straight line, which does not falsify the clinical evidence, the straight sedimentation line can be characterized by the tangent of the angle of inclination $\alpha$. This angle of inclination corresponds substantially to different pathological conditions.

Since the angle of inclination is identical for all points of the straight sedimentation line, a clinical statement can be made already at a very early point of time by measuring this angle of inclination. If the height of the blood column that is to be sedimented is standarized, then the method according to the invention can be compared with other methods of erythrocyte sedimentation.

The angle of inclination of the straight sedimentation line can simply be determined from its tangent (see FIG. 1 and 2) by means of a time or length measurement. The following methods of determination can be utilized:

a. Optical determination of the degree of sedimentation of the erythrocyte column within a specific period of time. Calculation of the angle of inclination by means of the C, D and T scales of a slide rule.

b. Optical determination by transfer of measurement points onto millimeter paper. The angle of inclination of the straight line created can then be read off with the aid of a printed angular graduation.

c. Electronic determination with the aid of photo cells. By means of simultaneous time measurement the angle of inclination is calculated electronically.

The method according to the invention offers the following advantages:

1. Only a few drops of capillary blood are required. Venipuncture is thus avoided.
2. Execution of the method is simple and results are rapidly obtained.
3. There is hardly the possibility of a methodical error, since dilution of the blood is not necessary.
4. For evaluating the result of the test only a number corresponding to the angle of inclination $\alpha$ is necessary.
5. Electronic evaluation is possible.
6. Erythrocyte sedimentation can be carried through more frequently. Thus a deterioration in the condition of a patient can be discovered more quickly.

BRIEF DESCRIPTION OF THE DRAWING

An embodiment of the micro-method according to the invention of erythrocyte sedimentation will now be described by way of example and with reference to the accompanying drawing, in which:

FIG. 1 is an elevational view of the apparatus for carrying out the proposed method, and FIG. 2 shows a coordinate system.

DESCRIPTION OF THE PREFERRED EMBODIMENT

FIG. 1 shows a heparinized glass capillary tube G filled with blood. Erythrocyte sedimentation has been carried through.

The settled erythrocyte column has the length H. Above the erythrocyte column the blood plasma or serum P can be seen to extend up to the original level of the blood within the capillary tube G.

The capillary tube G is sealed at its lower end by a cement plug K and stands upright in a block L with central bores M. A vertical plate R is secured to the rear side of the block L and is provided with horizontal lines D spaced 1 mm from each other. These lines D are only schematically indicated in FIG. 1. The millimeter graduation on the plate R permits a simple optical reading of the erythrocyte sedimentation values.

FIG. 2 shows a coordinate system (height Y of the erythrocyte column in relation to the time of sedimenta tion) with the straight sedimentation line S corresponding to the erythrocyte sedimentation according to FIG. 1.

The straight sedimentation line is expediently defined by means of the tangent of the angle of inclination $\alpha$ of the line. The angle $\alpha$ varies according to the pathological condition of the patient.

A standardized height of 7 cm forms the basis of the exemplary embodiment. The sedimentation occured within a time B (75 minutes) through a height A corresponding to the height of the blood plasma column.

The invention may be embodied in other specific forms without departing from the spirit or essential characteristics thereof. The embodiment is therefore to be considered in all respects as illustrated and not restrictive.

What is claimed is:

1. A micro-method of determining erythrocyte sedimentation in the blood of a patient, said method comprising
   a. introducing a blood sample into a vertical capillary tube having an anticoagulant heparin coating on the interior surface thereof,
   b. measuring the distance from the original level of the blood in said tube to the erythrocyte level at a predetermined time interval after the blood sample is introduced into the tube, and
   c. determining the angle of inclination of the straight sedimentation line in a plot of sedimentation distance against time as a measure of the pathological condition of said patient.

* * * * *